United States Patent
Green et al.

(10) Patent No.: US 9,383,338 B2
(45) Date of Patent: Jul. 5, 2016

(54) CORRECTION OF TIME OF FLIGHT MS ADC DATA ON PUSH BY PUSH BASIS

(71) Applicant: Micromass UK Limited, Wilmslow (GB)

(72) Inventors: Martin Raymond Green, Bowdon (GB); Steven Derek Pringle, Darwen (GB); Jason Lee Wildgoose, Stockport (GB); David J. Langridge, Macclesfield (GB)

(73) Assignee: Micromass UK Limited, Wilmslow (GB)

( * ) Notice: Subject to any disclaimer, the term of this patent is extended or adjusted under 35 U.S.C. 154(b) by 0 days.

(21) Appl. No.: 14/651,929

(22) PCT Filed: Dec. 13, 2013

(86) PCT No.: PCT/GB2013/053288
§ 371 (c)(1),
(2) Date: Jun. 12, 2015

(87) PCT Pub. No.: WO2014/091243
PCT Pub. Date: Jun. 19, 2014

(65) Prior Publication Data
US 2015/0316506 A1    Nov. 5, 2015

(30) Foreign Application Priority Data

Dec. 14, 2012 (GB) .................... 1222570.2
Jan. 2, 2013 (EP) ..................... 13150066

(51) Int. Cl.
*G01N 27/62* (2006.01)
*H01J 49/00* (2006.01)

(52) U.S. Cl.
CPC .......... *G01N 27/622* (2013.01); *H01J 49/0009* (2013.01); *H01J 49/0036* (2013.01)

(58) Field of Classification Search
USPC ......................................... 250/287, 281, 282
See application file for complete search history.

(56) References Cited

U.S. PATENT DOCUMENTS

| | | | |
|---|---|---|---|
| 6,229,142 B1 * | 5/2001 | Bateman | H01J 49/0036 250/287 |
| 7,474,394 B2 | 1/2009 | Hamamatsu et al. | |
| 8,374,799 B2 | 2/2013 | Ivosev | |
| 2007/0268171 A1 * | 11/2007 | Hidalgo | H01J 49/0031 341/155 |
| 2011/0226943 A1 | 9/2011 | Raether | |
| 2013/0181123 A1 | 7/2013 | Raether | |
| 2013/0338935 A1 | 12/2013 | Watanabe | |

FOREIGN PATENT DOCUMENTS

WO    2010/001973    1/2010

* cited by examiner

*Primary Examiner* — Kiet T Nguyen
(74) *Attorney, Agent, or Firm* — Diederiks & Whitelaw, PLC

(57) ABSTRACT

A method of mass spectrometry is disclosed comprising pulsing ions into a time of flight region and detecting the ions using an ion detector. The signal output from the ion detector is digitized to produce a digitized signal. The peak area $A_1$ and arrival time $T_1$ of the ion peak are determined and a degree to which the ion peak suffers from saturation is also determined. A corrected area $A'_1$ of the ion peak is then determined based upon the degree to which the ion peak was determined to suffer from saturation.

20 Claims, 7 Drawing Sheets

CORRECTION OF TIME OF FLIGHT MS ADC DATA ON PUSH BY PUSH BASIS

CROSS-REFERENCE TO RELATED APPLICATION

This application is the National Stage of International Application No. PCT/GB2013/053288, filed 13 Dec. 2013 which claims priority from and the benefit of United Kingdom patent application No. 1222570.2 filed on 14 Dec. 2012 and European patent application No. 13150066.2 filed 2 Jan. 2013. The entire contents of these applications are incorporated herein by reference.

BACKGROUND OF THE PRESENT INVENTION

Mass spectrometers comprising ion detection systems which employ Analogue to Digital Converters ("ADCs") are well known.

Mass spectrometers which utilise multiple gain ADCs or which use ADCs having an increased number of vertical bits (as technology continues to develop) are also well known.

It is known to extend the dynamic range by cascading multiple ADCs together at multiple gains. However, this approach requires additional ADCs to be provided which is relatively expensive.

US2011/0226943 (Räther) discloses a method of increasing the dynamic range of a mass spectrometer by replacing measured saturated intensity values with a corrected intensity value. The corrected values are summed to provide a sum spectrum. Such an approach does improve the dynamic range of a mass spectrometer. However, the improvement in dynamic range is limited.

It is desired to provide an improved mass spectrometer and method of mass spectrometry.

SUMMARY OF THE PRESENT INVENTION

According to an aspect of the present invention there is provided a method of mass spectrometry comprising:

pulsing first ions into a time of flight region and detecting the first ions using an ion detector;

digitizing a first signal output from the ion detector to produce a first digitized signal, determining a first area $A_1$ and optionally a first ion arrival time $T_1$ of a first ion peak in the first digitized signal, determining a degree to which the first ion peak suffers from saturation and determining a first corrected area $A'_1$ of the first ion peak based upon the degree to which the first ion peak was determined to suffer from saturation;

pulsing second ions into the time of flight region and detecting the second ions using the ion detector; and digitizing a second signal output from the ion detector to produce a second digitized signal, determining a second area $A_2$ and optionally a second ion arrival time $T_2$ of a second ion peak in the second digitized signal, optionally determining a degree to which the second ion peak suffers from saturation and optionally determining a second corrected area $A'_2$ of the second ion peak based upon the degree to which the second ion peak was determined to suffer from saturation.

US 2011/0226943 (Räther) discloses a method wherein ion signals that drive an ADC in saturation in an individual time of flight spectrum are replaced with corrected values. The corrected values are derived from the number of values of the ion signal in saturation. As shown and described with reference to FIG. 2 of US 2011/0226943, if for example a single ADC time bin is saturated then the true intensity of the ion signal may only just exceed the saturation level but if a greater number of ADC time bins are saturated then the true intensity of the ion signal is likely to be correspondingly higher.

As detailed in paragraph [0018] of US 2011/0226943, the known approach is to add a single intensity value to a central ADC time bin of a sequence of measured intensity values which are in saturation. The single intensity value which is added is determined using a look-up table and the intensity value varies in dependence upon the number of intensity values which are measured as being in saturation.

The present invention differs from the disclosure in US 2011/0226943 in that in contrast to the approach disclosed in US 2011/0226943 according to the present invention the area of ion peaks rather than the intensity of ion peaks are determined.

Figure 5:
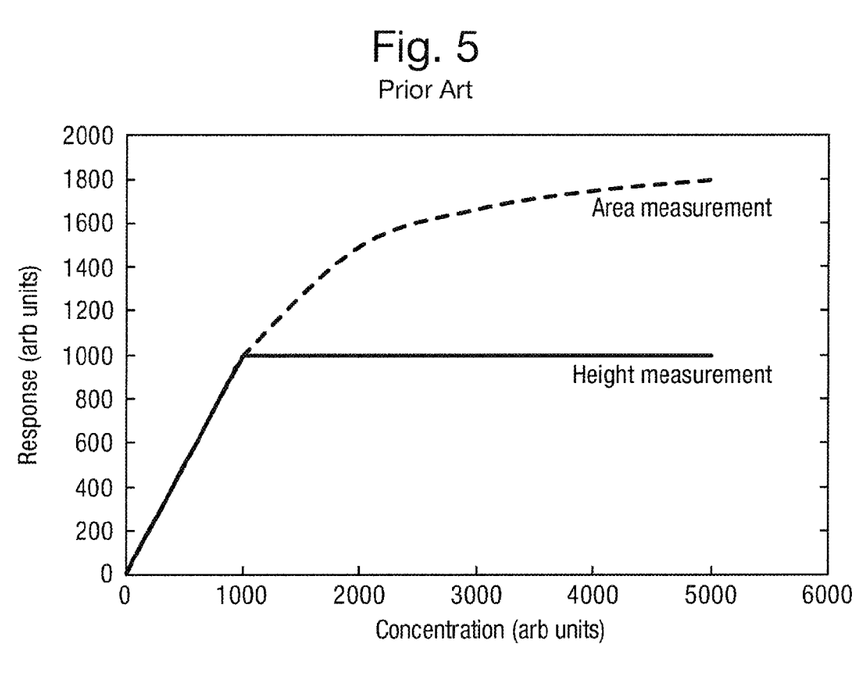
FIG. 5 shows how measuring the area of an ion peak results in improved dynamic range compared with measuring the height or maximum intensity of an ion peak.

Furthermore, the present invention is particularly advantageous compared with the arrangement disclosed in US 2011/0226943 in that as will be described in the present application in more detail with reference, for example, to FIG. 5 it is particularly advantageous to measure the area of ion peaks rather than their intensity. Measuring the area of ion peaks rather than their intensity results in a nearly two-fold improvement in the dynamic range of the ion detector. In order to illustrate this, an ion peak having the profile of an isosceles triangle may be considered. As will be appreciated by those skilled in the art, as the intensity of the ion signal increases both the height and the base area of the ion signal will increase. The base area of the ion signal below the saturation level will continue to increase even when the height of the triangle exceeds the saturation level.

US 2011/0226943 does not teach or suggest the method of peak area detection and replacement of ion peak areas with corrected ion peak areas according to the present invention.

According to the present invention Time of Flight ADC data is corrected on a push by push basis. The term "push by push" will be understood by those skilled in the art as relating to individual time of flight spectra. As will be understood by those skilled in the art Time of Flight data is commonly displayed at a frequency of 1 to 100 spectra per second (commonly referred to as the integration time). However, in reality Time of Flight mass spectrometers operate at much higher frequencies e.g. 1 to 100 kHz. The displayed data is therefore a combination of multiple time of flight spectra. For example, a 0.1 s time of flight integration time will comprise a combination of 10,000 individual 100 kHz time of flight spectra. The combining function may be achieved in many different ways including histogramming and averaging.

The act of combining the data according to the known approach loses some of the information that would otherwise have been available if the data had been interrogated on a push by push basis in a manner in accordance with the present invention. For example, signal changes within the integration time due to statistical effects or due to transmission effects may lead to individual peaks within individual time of flight spectra saturating. A particularly advantageous aspect of the present invention is therefore that an individual time of flight spectrum which suffers from saturation can be directly identified, measured and corrected on a push by push basis with the result that the correction is likely to be more precise than simply estimating the degree of saturation based upon thousands of combined mass spectra.

In the present application reference to determining a "centroid" of an ion peak is intended to refer to the process wherein an algorithm or control system determines both the arrival time and the area of the ion peak. The process of determining the centroid involves determining the arrival time and intensity of an ion peak based upon multiple digitization points across the ion peak. Reference in the present application to determining a centroid is intended to cover approaches which, for example, involve de-convolution.

The preferred embodiment provides the capability to extend the dynamic range of an ADC based ion detection system employed in a Time of Flight mass spectrometer by peak detecting events on a push by push basis wherein the amount or degree of saturation is preferably determined on a push by push basis. The area of the peak or the centroid associated with the event is preferably corrected based upon the amount or degree of saturation which is determined to have occurred. The resulting time and intensity pairs from multiple events are preferably combined resulting in a final mass spectrum which advantageously exhibits an increased dynamic range compared with conventional approaches.

The peak detecting ADC preferably determines Time of Flight event arrival times to sub ADC bin precision. The control system preferably determines Time of Flight event intensities by determining the area or centroid of the ion peak and preferably compensates for any degree of saturation of a Time of Flight event on a push by push basis.

The preferred embodiment results in a Time of Flight mass spectrometer employing an ADC based ion detection system which has an improved dynamic range.

It is apparent, therefore, that the present invention is particularly advantageous compared with conventional ion detection systems.

The first digitized signal preferably comprises a plurality of first intensity values distributed amongst a plurality of first time or other bins.

The step of determining a degree to which the first ion peak suffers from saturation preferably comprises determining the number of first time or other bins having intensity values indicative of saturation.

The step of determining a first corrected area $A'_1$ further comprises preferably adjusting or increasing the first area $A_1$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

The preferred method preferably further comprises determining a first corrected ion arrival time $T'_1$ of the first ion peak based upon the degree to which the first ion peak was determined to suffer from saturation.

The second digitized signal preferably comprises a plurality of second intensity values distributed amongst a plurality of second time or other bins.

The step of determining a degree to which the second ion peak suffers from saturation preferably comprises determining the number of second time or other bins having intensity values indicative of saturation.

The step of determining a second corrected area $A'_2$ preferably further comprises adjusting or increasing the second area $A_2$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

The preferred method preferably further comprises determining a second corrected ion arrival time $T'_2$ of the second ion peak based upon the degree to which the second ion peak was determined to suffer from saturation.

The method preferably further comprises:
pulsing third ions into the time of flight region and detecting the third ions using the ion detector; and
digitizing a third signal output from the ion detector to produce a third digitized signal, determining a third area $A_3$ and optionally a third ion arrival time $T_3$ of a third ion peak in the third digitized signal, optionally determining a degree to which the third ion peak suffers from saturation and optionally determining a third corrected area $A'_3$ of the third ion peak based upon the degree to which the third ion peak was determined to suffer from saturation.

The third digitized signal preferably comprises a plurality of third intensity values distributed amongst a plurality of third time or other bins.

The step of determining a degree to which the third ion peak suffers from saturation preferably comprises determining the number of third time or other bins having intensity values indicative of saturation.

The step of determining a third corrected area $A'_3$ preferably further comprises adjusting or increasing the third area $A_3$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

The method preferably further comprises determining a third corrected ion arrival time $T'_3$ of the third ion peak based upon the degree to which the third ion peak was determined to suffer from saturation.

The method preferably further comprises:
pulsing fourth ions into the time of flight region and detecting the fourth ions using the ion detector; and
digitizing a fourth signal output from the ion detector to produce a fourth digitized signal, determining a fourth area $A_4$ and optionally a fourth ion arrival time $T_4$ of a fourth ion peak in the fourth digitized signal, optionally determining a degree to which the fourth ion peak suffers from saturation and optionally determining a fourth corrected area $A'_4$ of the fourth ion peak based upon the degree to which the fourth ion peak was determined to suffer from saturation.

The fourth digitized signal preferably comprises a plurality of fourth intensity values distributed amongst a plurality of fourth time or other bins.

The step of determining a degree to which the fourth ion peak suffers from saturation preferably comprises determining the number of fourth time or other bins having intensity values indicative of saturation.

The step of determining a fourth corrected area $A'_4$ preferably further comprises adjusting or increasing the fourth area $A_4$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

The method preferably further comprises determining a fourth corrected ion arrival time $T'_4$ of the fourth ion peak based upon the degree to which the fourth ion peak was determined to suffer from saturation.

The method preferably further comprises:
pulsing fifth or further ions into the time of flight region and detecting the fifth or further ions using the ion detector; and
digitizing a fifth or further signal output from the ion detector to produce a fifth or further digitized signal, determining a fifth or further area $A_5$ and optionally a fifth or further ion arrival time $T_5$ of a fifth or further ion peak in the fifth or further digitized signal, optionally determining a degree to which the fifth or further ion peak suffers from saturation and optionally determining a fifth or further corrected area $A'_5$ of the fifth or further ion peak based upon the degree to which the fifth or further ion peak was determined to suffer from saturation.

The fifth or further digitized signal preferably comprises a plurality of fifth or further intensity values distributed amongst a plurality of fifth or further time or other bins.

The step of determining a degree to which the fifth or further ion peak suffers from saturation preferably comprises determining the number of fifth or further time or other bins having values indicative of saturation.

The step of determining a fifth or further corrected area $A'_5$ preferably further comprises adjusting or increasing the fifth or further area $A_5$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

The method preferably further comprises determining a fifth or further corrected ion arrival time $T'_5$ of the fifth or further ion peak based upon the degree to which the fifth or further ion peak was determined to suffer from saturation.

The method preferably further comprises combining: (i) the first corrected area $A'_1$ and the first ion arrival time $T_1$; and/or (ii) the second corrected area $A'_2$ and the second ion arrival time $T_2$; and/or (iii) the third corrected area $A'_3$ and the third ion arrival time $T_3$; and/or (iv) the fourth corrected area $A'_4$ and the fourth ion arrival time $T_4$, and/or (v) the fifth or further corrected area $A'_5$ and the fifth or further ion arrival time $T_5$ to produce a composite intensity-ion arrival time spectrum.

The method preferably further comprises combining: (i) the first corrected area $A'_1$ and the first corrected ion arrival time $T'_1$; and/or (ii) the second corrected area $A'_2$ and the second corrected ion arrival time $T'_2$; and/or (iii) the third corrected area $A'_3$ and the third corrected ion arrival time $T'_3$; and/or (iv) the fourth corrected area $A'_4$ and the fourth corrected ion arrival time $T'_4$; and/or (v) the fifth or further corrected area $A'_5$ and the fifth or further corrected ion arrival time $T'_5$ to produce a composite intensity-ion arrival time spectrum.

The ion detector is preferably coupled to an Analogue to Digital Converter.

The step of digitizing the first signal and/or the second signal and/or the third signal and/or the fourth signal and/or the fifth or further signal is preferably performed by an Analogue to Digital Converter.

The method preferably comprises correcting the area and optionally arrival time of ion peaks in digitized signals on a push-by-push basis.

The step of determining the first corrected area $A'_1$ and/or the second corrected area $A'_2$ and/or the third corrected area $A'_3$ and/or the fourth corrected area $A'_4$ and/or the fifth or further corrected area $A'_5$ preferably comprises determining one or more additional factors in addition to the degree to which the first, second, third, fourth, fifth or further ion peak (s) were determined to suffer from saturation.

The step of determining the first corrected ion arrival time $T'_1$ and/or the second corrected ion arrival time $T'_2$ and/or the third corrected ion arrival time $T'_3$ and/or the fourth corrected ion arrival time $T'_4$ and/or the fifth or further corrected ion arrival time $T'_5$ preferably further comprises determining one or more additional factors in addition to the degree to which the first, second, third, fourth, fifth or further ion peak(s) were determined to suffer from saturation.

The one or more additional factors are preferably selected from the group consisting of: (i) the area of the first, second, third, fourth, fifth or further ion peak optionally within an event window; (ii) the width of the first, second, third, fourth, fifth or further ion peak at a first intensity and the width of the first, second, third, fourth, fifth or further ion peak at a second intensity optionally within an event window; (iii) the skew of the first, second, third, fourth, fifth or further ion peak optionally within an event window; (iv) the kurtosis of the first, second, third, fourth, fifth or further ion peak optionally within an event window; (v) a measurement of the first order differential of the first, second, third, fourth, fifth or further ion peak optionally across the whole of an event window; (vi) a measurement of the second or higher order differential of the first, second, third, fourth, fifth or further ion peak optionally across the whole of an event window; (vii) a measurement of the leading edge profile of the first, second, third, fourth, fifth or further ion peak optionally within an event window; and (viii) a measurement of the trailing edge profile of the first, second, third, fourth, fifth or further ion peak optionally within an event window.

According to an aspect of the present invention there is provided a mass spectrometer comprising:
a time of flight region and an ion detector; and
a control system arranged and adapted:
(i) to pulse first ions into the time of flight region and to detect the first ions using the ion detector;
(ii) to digitize a first signal output from the ion detector to produce a first digitized signal, to determine a first area $A_1$ and optionally a first ion arrival time $T_1$ of a first ion peak in the first digitized signal, to determine a degree to which the first ion peak suffers from saturation and to determine a first corrected area $A'_1$ of the first ion peak based upon the degree to which the first ion peak was determined to suffer from saturation;
(iii) to pulse second ions into the time of flight region and to detect the second ions using the ion detector; and
(iv) to digitize a second signal output from the ion detector to produce a second digitized signal, to determine a second area $A_2$ and optionally a second ion arrival time $T_2$ of a second ion peak in the second digitized signal, optionally to determine a degree to which the second ion peak suffers from saturation and optionally to determine a second corrected area $A'_2$ of the second ion peak based upon the degree to which the second ion peak was determined to suffer from saturation.

The ion detector is preferably coupled to an Analogue to Digital Converter.

The control system is preferably arranged and adapted to correct the area and optionally arrival time of ion peaks in digitized signals on a push-by-push basis.

The control system is preferably arranged and adapted to determine a first corrected area $A'_1$ and/or a second corrected area $A'_2$ by determining one or more additional factors in addition to the degree to which the first ion peak and/or the second ion peak was determined to suffer from saturation.

The control system is preferably arranged and adapted to determine the first corrected ion arrival time $T'_1$ and/or the second corrected ion arrival time $T'_2$ by determining one or more additional factors in addition to the degree to which the first ion peak and/or the second ion peak was determined to suffer from saturation.

The one or more additional factors are preferably selected from the group consisting of: (i) the area of the first and/or second ion peak optionally within an event window; (ii) the width of the first and/or second ion peak at a first intensity and the width of the first and/or second ion peak at a second intensity optionally within an event window; (iii) the skew of the first and/or second ion peak optionally within an event window; (iv) the kurtosis of the first and/or second ion peak optionally within an event window; (v) a measurement of the first order differential of the first and/or second ion peak optionally across the whole of an event window; (vi) a measurement of the second or higher order differential of the first and/or second ion peak optionally across the whole of an event window; (vii) a measurement of the leading edge profile of the first and/or second ion peak optionally within an event window; and (viii) a measurement of the trailing edge profile of the first and/or second ion peak optionally within an event window.

According to an aspect of the present invention there is provided a method of mass spectrometry comprising:

pulsing first ions into a time of flight region and detecting the first ions using an ion detector;

digitizing a first signal output from the ion detector to produce a first digitized signal, determining a first ion arrival time $T_1$ and optionally a first area $A_1$ of a first ion peak in the first digitized signal, determining a degree to which the first ion peak suffers from saturation and determining a first corrected ion arrival time $T'_1$ of the first ion peak based upon the degree to which the first ion peak was determined to suffer from saturation;

pulsing second ions into the time of flight region and detecting the second ions using the ion detector; and digitizing a second signal output from the ion detector to produce a second digitized signal, determining a second ion arrival time $T_2$ and optionally a second area $A_2$ of a second ion peak in the second digitized signal, optionally determining a degree to which the second ion peak suffers from saturation and optionally determining a second corrected ion arrival time $T'_2$ of the second ion peak based upon the degree to which the second ion peak was determined to suffer from saturation.

The ion detector is preferably coupled to an Analogue to Digital Converter.

The method preferably comprises correcting the area and optionally arrival time of ion peaks in digitized signals on a push-by-push basis.

The step of determining the first corrected area $A'_1$ and/or thesecond corrected area $A'_2$ preferably further comprises determining one or more additional factors in addition to the degree to which the first ion peak and/or the second ion peak was determined to suffer from saturation.

The step of determining the first corrected ion arrival time $T'_1$ and/or the second corrected ion arrival time $T'_2$ preferably further comprises determining one or more additional factors in addition to the degree to which the first ion peak and/or sais second ion peak was determined to suffer from saturation.

The one or more additional factors are preferably selected from the group consisting of: (i) the area of the first and/or second ion peak optionally within an event window; (ii) the width of the first and/or second ion peak at a first intensity and the width of the first and/or second ion peak at a second intensity optionally within an event window; (iii) the skew of the first and/or second ion peak optionally within an event window; (iv) the kurtosis of the first and/or second ion peak optionally within an event window; (v) a measurement of the first order differential of the first and/or second ion peak optionally across the whole of an event window; (vi) a measurement of the second or higher order differential of the first and/or second ion peak optionally across the whole of an event window; (vii) a measurement of the leading edge profile of the first and/or second ion peak optionally within an event window; and (viii) a measurement of the trailing edge profile of the first and/or second ion peak optionally within an event window.

According to an aspect of the present invention there is provided a mass spectrometer comprising:

a time of flight region and an ion detector; and a control system arranged and adapted:

(i) to pulse first ions into the time of flight region and to detect the first ions using an ion detector;

(ii) to digitize a first signal output from the ion detector to produce a first digitized signal, to determine a first ion arrival time $T_1$ and optionally a first area $A_1$ of a first ion peak in the first digitized signal, to determine a degree to which the first ion peak suffers from saturation and to determine a first corrected ion arrival time $T'_1$ of the first ion peak based upon the degree to which the first ion peak was determined to suffer from saturation;

(iii) to pulse second ions into the time of flight region and to detect the second ions using the ion detector; and (iv) to digitize a second signal output from the ion detector to produce a second digitized signal, to determine a second ion arrival time $T_2$ and optionally a second area $A_2$ of a second ion peak in the second digitized signal, optionally to determine a degree to which the second ion peak suffers from saturation and optionally to determine a second corrected ion arrival time $T'_2$ of the second ion peak based upon the degree to which the second ion peak was determined to suffer from saturation.

The ion detector is preferably coupled to an Analogue to Digital Converter.

The control system is preferably arranged and adapted to correct the area and optionally arrival time of ion peaks in digitized signals on a push-by-push basis.

The control system is preferably arranged and adapted to determine a first corrected area $A'_1$ and/or a second corrected area $A'_2$ by determining one or more additional factors in addition to the degree to which the first ion peak was determined to suffer from saturation.

The control system is preferably arranged and adapted to determine the first corrected ion arrival time $T'_1$ and/or the second corrected ion arrival time $T'_2$ by determining one or more additional factors in addition to the degree to which the first ion peak was determined to suffer from saturation.

The one or more additional factors are preferably selected from the group consisting of: (i) the area of the first and/or second ion peak optionally within an event window; (ii) the width of the first and/or second ion peak at a first intensity and the width of the first and/or second ion peak at a second intensity optionally within an event window; (iii) the skew of the first and/or second ion peak optionally within an event window; (iv) the kurtosis of the first and/or second ion peak optionally within an event window; (v) a measurement of the first order differential of the first and/or second ion peak optionally across the whole of an event window; (vi) a measurement of the second or higher order differential of the first and/or second ion peak optionally across the whole of an event window; (vii) a measurement of the leading edge profile of the first and/or second ion peak optionally within an event window; and (viii) a measurement of the trailing edge profile of the first and/or second ion peak optionally within an event window.

According to an aspect of the present invention there is provided a method of mass spectrometry comprising:

pulsing first ions into a time of flight region and detecting the first ions using an ion detector;

digitizing a first signal output from the ion detector to produce a first digitized signal, determining a first ion mass or mass to charge ratio $M_1$ and optionally a first area $A_1$ of a first ion peak in the first digitized signal, determining a degree to which the first ion peak suffers from saturation and determining a first corrected ion mass or mass to charge ratio $M'_1$ of the first ion peak based upon the degree to which the first ion peak was determined to suffer from saturation;

pulsing second ions into the time of flight region and detecting the second ions using the ion detector; and digitizing a second signal output from the ion detector to produce a second digitized signal, determining a second ion mass or mass to charge ratio $M_2$ and optionally a second area $A_2$ of a second ion peak in the second digitized signal, optionally determining a degree to which the second ion peak suffers from saturation and optionally determining a second corrected ion mass or mass to charge ratio $M'_2$ of the second ion peak based upon the degree to which the second ion peak was determined to suffer from saturation.

The ion detector is preferably coupled to an Analogue to Digital Converter.

The method preferably comprises correcting the area and optionally arrival time of ion peaks in digitized signals on a push-by-push basis.

According to an aspect of the present invention there is provided a mass spectrometer comprising:

a time of flight region and an ion detector; and
a control system arranged and adapted:
(i) to pulse first ions into the time of flight region and to detect the first ions using an ion detector;
(ii) to digitize a first signal output from the ion detector to produce a first digitized signal, to determine a first ion mass or mass to charge ratio $M_1$ and optionally a first area $A_1$ of a first ion peak in the first digitized signal, to determine a degree to which the first ion peak suffers from saturation and to determine a first corrected ion mass or mass to charge ratio $M'_1$ of the first ion peak based upon the degree to which the first ion peak was determined to suffer from saturation;
(iii) to pulse second ions into the time of flight region and to detect the second ions using the ion detector; and
(iv) to digitize a second signal output from the ion detector to produce a second digitized signal, to determine a second ion mass or mass to charge ratio $M_2$ and optionally a second area $A_2$ of a second ion peak in the second digitized signal, optionally to determine a degree to which the second ion peak suffers from saturation and optionally to determine a second corrected ion mass or mass to charge ratio $M'_2$ of the second ion peak based upon the degree to which the second ion peak was determined to suffer from saturation.

The ion detector is preferably coupled to an Analogue to Digital Converter.

The control system is preferably arranged and adapted to correct the area and optionally arrival time of ion peaks in digitized signals on a push-by-push basis.

According to an aspect of the present invention there is provided a method of mass spectrometry comprising:
(i) pulsing ions into a Time of Flight region and detecting the ions using an ion detector and an associated Analogue to Digital Converter;
(ii) determining one or more area values and/or one or more arrival time values and/or one or more mass or mass to charge ratio values of one or more ion peaks;
(iii) determining the number of intensity values within an event window which are at a maximum or are otherwise saturated;
(iv) adjusting the one or more area values and/or the one or more arrival time values and/or the one or more mass or mass to charge ratio values dependent upon the number of intensity values within the event window which were determined to be at a maximum or which were otherwise saturated;

repeating steps (i)-(iv) multiple times; and then optionally generating a composite mass spectrum from a plurality of adjusted area values and/or a plurality of adjusted arrival time values and/or a plurality of adjusted mass or mass to charge ratio values.

The method preferably comprises correcting the area and/or arrival time and/or mass or mass to charge ratio of ion peaks in digitized signals on a push-by-push basis.

According to an aspect of the present invention there is provided a mass spectrometer comprising:

a Time of Flight mass analyser comprising a Time of Flight region, an ion detector and an associated Analogue to Digital Converter; and a control system arranged and adapted repeatedly:
(i) to pulse ions into the Time of Flight region and to detect the ions using the ion detector and the associated Analogue to Digital Converter;
(ii) to determine one or more area values and/or one or more arrival time values and/or one or more mass or mass to charge ratio values of one or more ion peaks;
(iii) to determine the number of intensity values within an event window which are at a maximum or are otherwise saturated; and
(iv) to adjust the one or more area values and/or the one or more arrival time values and/or the one or more mass or mass to charge ratio values dependent upon the number of intensity values within the event window which were determined to be at a maximum or which were otherwise saturated;

wherein the control system is optionally further arranged and adapted to generate a composite mass spectrum from a plurality of adjusted area values and/or a plurality of adjusted arrival time values and/or a plurality of adjusted mass or mass to charge ratio values.

The control system is preferably arranged and adapted to correct the area and/or arrival time and/or mass or mass to charge ratio of ion peaks in digitized signals on a push-by-push basis.

According to an aspect of the present invention there is provided a method of mass spectrometry comprising:

digitizing a signal output from an ion detector;

determining the number of intensity values which are at a maximum or which are otherwise saturated; and adjusting on a push-by-push basis one or more area values and/or one or more arrival time values and/or one or more mass or mass to charge ratio values dependent upon the number of intensity values which are determined to be at a maximum or are otherwise saturated and optionally upon one or more additional factors.

According to an aspect of the present invention there is provided a mass spectrometer comprising:

a device arranged and adapted to digitize a signal output from an ion detector;

a device arranged and adapted to determine the number of intensity values which are at a maximum or which are otherwise saturated; and a device arranged and adapted to adjust on a push-by-push basis one or more area values and/or one or more arrival time values and/or one or more mass or mass to charge ratio values dependent upon the number of intensity values which are determined to be at a maximum or are otherwise saturated and optionally upon one or more additional factors.

According to an aspect of the present invention there is provided a method of mass spectrometry comprising:

digitizing a signal output from an ion detector using an Analogue to Digital Converter to produce a plurality of time and intensity values;

determining an area or centroid of an ion peak from the intensity values;

determining the number of intensity values which have a maximum or saturated value;

increasing or adjusting the determined area or centroid of the ion peak by a factor which is dependent upon the number of intensity values determined to have a maximum or saturated value and optionally upon one or more additional factors.

The method preferably comprises correcting the area and/or arrival time and/or mass or mass to charge ratio of ion peaks in digitized signals on a push-by-push basis.

According to an aspect of the present invention there is provided a mass spectrometer comprising:

an Analogue to Digital Converter arranged and adapted to digitize a signal output from an ion detector to produce a plurality of time and intensity values;

a device arranged and adapted to determine an area or centroid of an ion peak from the intensity values;

a device arranged and adapted to determine the number of intensity values which have a maximum or saturated value;

a device arranged and adapted to increase or adjust the determined area or centroid of the ion peak by a factor which is dependent upon the number of intensity values determined to have a maximum or saturated value and optionally upon one or more additional factors.

The mass spectrometer is preferably arranged and adapted to correct the area and/or arrival time and/or mass or mass to charge ratio of ion peaks in digitized signals on a push-by-push basis.

According to an aspect of the present invention there is provided a method of mass spectrometry comprising:

determining an area or centroid of an ion peak;

determining the number of intensity values, optionally within an event window, which have either: (i) a maximum or saturated value; and/or (ii) a value below a maximum or saturated value; and correcting the determined area or centroid of the ion peak dependent upon either: (i) the number of intensity values determined to have a maximum or saturated value; and/or (ii) the number of intensity values determined to have a value below a maximum or saturated value; and optionally upon one or more additional factors.

The method preferably comprises correcting the area and/or arrival time and/or mass or mass to charge ratio of ion peaks in digitized signals on a push-by-push basis.

According to an aspect of the present invention there is provided a mass spectrometer comprising:

a device arranged and adapted to determine an area or centroid of an ion peak;

a device arranged and adapted to determine the number of intensity values, optionally within an event window, which have either: (i) a maximum or saturated value; and/or (ii) a value below a maximum or saturated value; and a device arranged and adapted to correct the determined area or centroid of the ion peak dependent upon either: (i) the number of intensity values determined to have a maximum or saturated value; and/or (ii) the number of intensity values determined to have a value below a maximum or saturated value; and optionally upon one or more additional factors.

The mass spectrometer is preferably arranged and adapted to correct the area and/or arrival time and/or mass or mass to charge ratio of ion peaks in digitized signals on a push-by-push basis.

According to an aspect of the present invention there is provided a method of mass spectrometry comprising:

correcting or adjusting a determined area or centroid of an ion peak dependent upon the number of intensity values, optionally within an event window, which have either: (i) a maximum or saturated value; and/or (ii) a value below a maximum or saturated value; and optionally upon one or more additional factors.

The method preferably comprises correcting the area and/or arrival time and/or mass or mass to charge ratio of ion peaks in digitised signals on a push-by-push basis.

According to an aspect of the present invention there is provided a mass spectrometer comprising:

a device arranged and adapted to correct or adjust a determined area or centroid of an ion peak dependent upon the number of intensity values, optionally within an event window, which have either: (i) a maximum or saturated value; and/or (ii) a value below a maximum or saturated value; and optionally upon one or more additional factors.

The mass spectrometer is preferably arranged and adapted to correct the area and/or arrival time and/or mass or mass to charge ratio of ion peaks in digitized signals on a push-by-push basis.

The one or more additional factors are preferably selected from the group consisting of: (i) the degree to which an ion peak was determined to suffer from saturation i.e. the number of saturated ADC time bins; (ii) the area of the ion peak optionally within an event window; (iii) the width of the ion peak at a first intensity and the width of ion peak at a second intensity optionally within an event window; (iv) the skew of the ion peak optionally within an event window; (v) the kurtosis of the ion peak optionally within an event window; (vi) a measurement of the first order differential of the ion peak optionally across the whole of an event window; (vii) a measurement of the second or higher order differential of the ion peak optionally across the whole of an event window; (viii) a measurement of the leading edge profile of the ion peak optionally within an event window; and (ix) a measurement of the trailing edge profile of the ion peak optionally within an event window.

According to another aspect of the present invention there is provided a method of mass spectrometry comprising:

pulsing first ions into a time of flight region and detecting the first ions using an ion detector;

digitizing a first signal output from the ion detector to produce a first digitized signal, determining a first area $A_1$ and optionally a first ion arrival time $T_1$ of a first ion peak in the first digitized signal and determining a first corrected area $A'_1$ of the first ion peak based upon two or more factors;

pulsing second ions into the time of flight region and detecting the second ions using the ion detector; and digitizing a second signal output from the ion detector to produce a second digitized signal, determining a second area $A_2$ and optionally a second ion arrival time $T_2$ of a second ion peak in the second digitized signal, optionally determining a degree to which the second ion peak suffers from saturation and optionally determining a second corrected area $A'_2$ of the second ion peak based upon two or more factors.

The two or more factors are preferably selected from the group consisting of: (i) the degree to which the first ion peak and/or the second ion peak was determined to suffer from saturation; (ii) the area of the first and/or second ion peak optionally within an event window; (iii) the width of the first and/or second ion peak at a first intensity and the width of the first and/or second ion peak at a second intensity optionally within an event window; (iv) the skew of the first and/or second ion peak optionally within an event window; (v) the kurtosis of the first and/or second ion peak optionally within an event window; (vi) a measurement of the first order differential of the first and/or second ion peak optionally across the whole of an event window; (vii) a measurement of the second or higher order differential of the first and/or second ion peak optionally across the whole of an event window; (viii) a measurement of the leading edge profile of the first and/or second ion peak optionally within an event window; and (ix) a measurement of the trailing edge profile of the first and/or second ion peak optionally within an event window.

According to another aspect of the present invention there is provided a mass spectrometer comprising:

a time of flight region and an ion detector; and a control system arranged and adapted:

(i) to pulse first ions into the time of flight region and to detect the first ions using the ion detector;

(ii) to digitize a first signal output from the ion detector to produce a first digitized signal, to determine a first area $A_1$ and optionally a first ion arrival time $T_1$ of a first ion peak in the first digitized signal and to determine a first corrected area $A'_1$ of the first ion peak based upon two or more factors;

(iii) to pulse second ions into the time of flight region and to detect the second ions using the ion detector; and (iv) to digitize a second signal output from the ion detector to produce a second digitized signal, to determine a second area $A_2$ and optionally a second ion arrival time $T_2$ of a second ion peak in the second digitized signal and optionally to determine a second corrected area $A'_2$ of the second ion peak based upon two or more factors.

The two or more factors are preferably selected from the group consisting of: (i) the degree to which the first ion peak and/or the second ion peak was determined to suffer from saturation; (ii) the area of the first and/or second ion peak optionally within an event window; (iii) the width of the first and/or second ion peak at a first intensity and the width of the first and/or second ion peak at a second intensity optionally within an event window; (iv) the skew of the first and/or second ion peak optionally within an event window; (v) the kurtosis of the first and/or second ion peak optionally within an event window; (vi) a measurement of the first order differential of the first and/or second ion peak optionally across the whole of an event window; (vii) a measurement of the second or higher order differential of the first and/or second ion peak optionally across the whole of an event window; (viii) a measurement of the leading edge profile of the first and/or second ion peak optionally within an event window; and (ix) a measurement of the trailing edge profile of the first and/or second ion peak optionally within an event window.

BRIEF DESCRIPTION OF THE DRAWINGS

Various embodiments of the present invention together with other arrangements given for illustrative purposes only will now be described, by way of example only, and with reference to the accompanying drawings in which.

DETAILED DESCRIPTION OF PREFERRED EMBODIMENTS

It is known to operate a Time of Flight mass spectrometer which employs ADCs in an averager mode. In this mode of operation the ADC is arranged to digitize the analogue signal received from an ion detection device (e.g. a MCP or electron multiplier) above a predefined threshold on a push by push basis. The digitized signals from multiple pushes are combined. The resultant peak widths represent a convolution of both the arrival time distribution ("ATD") and the analogue peak width and this results in relatively broad mass spectral peaks which have relatively low resolution.

Recent advances in electronics have facilitated the processing of Time of Flight data on a push by push basis i.e. individual time of flight mass spectra. It is known, for example, to operate fast running algorithms on Field Programmable Gate Arrays ("FPGAs") to peak detect Time of Flight events and then to assign a time and intensity value to the event on a push by push basis. Time and intensity values from multiple pushes are combined and the resultant peak widths are more representative of the ATD than the known averager method described above. This approach can result in improved resolution without loss in dynamic range compared with the averager approach.

Figure 1:
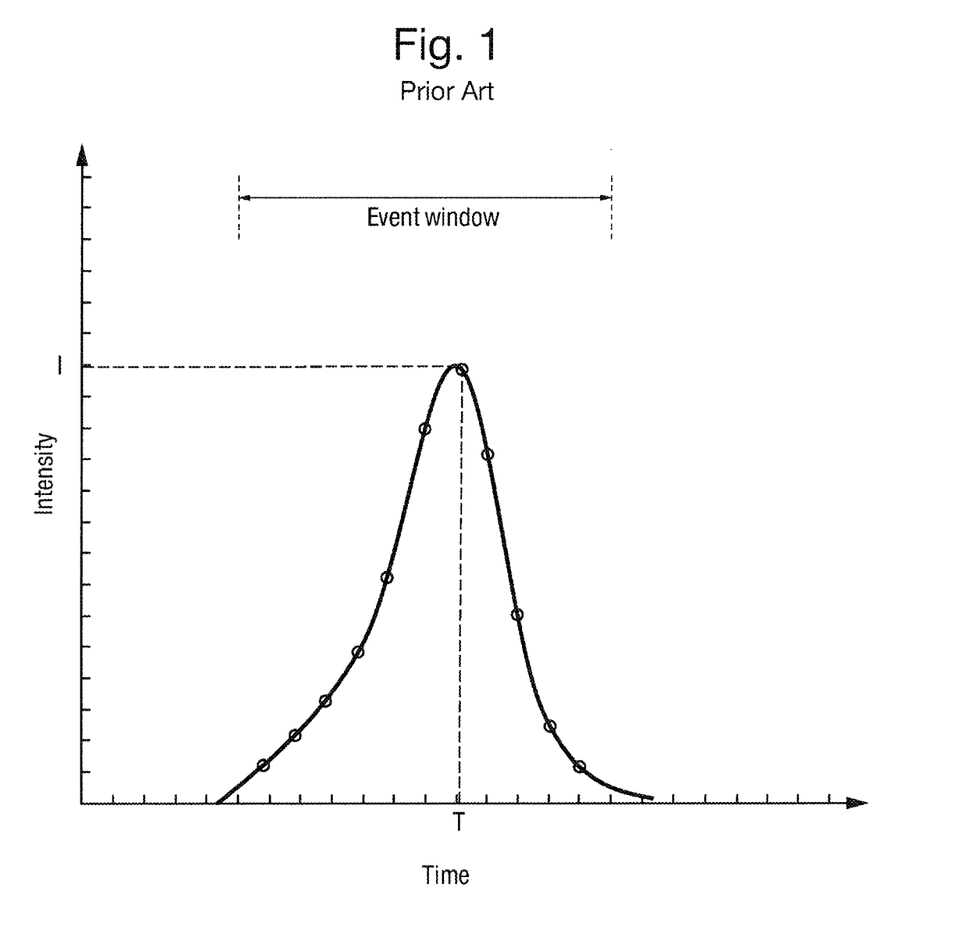
FIG. 1 shows an analogue signal which has been digitized in a conventional manner into a series of time and intensity values.

Various methods of assigning a time and intensity value to an ion peak are known. One approach is illustrated in FIG. 1 and comprises assigning the time and intensity of the maximum point within a peak detection or event window. The analogue signal (i.e. the continuous line in FIG. 1) is digitized resulting in a series of time and intensity values (represented by the circles shown in FIG. 1).

The FPGA algorithms determine that an event has occurred and is contained within the event window. The maximum intensity point within the event window is then determined and a time T and intensity I value are assigned to the event. Time and intensity values from multiple pushes are combined to form a final composite mass spectrum.

The above approach reduces the contribution of the analogue peak width to the final peak width. However, this approach still has a number of drawbacks. For example, the act of assigning the arrival time to the nearest time bin can compromise the mass accuracy and resolution particularly in cases where the ATD is significantly less than the analogue peak width. Another problem occurs when the analogue signal amplitude is beyond the vertical limit of the ADC i.e. when saturation occurs. This effect will be described in more detail below with reference to FIG. 2.

Figure 2:
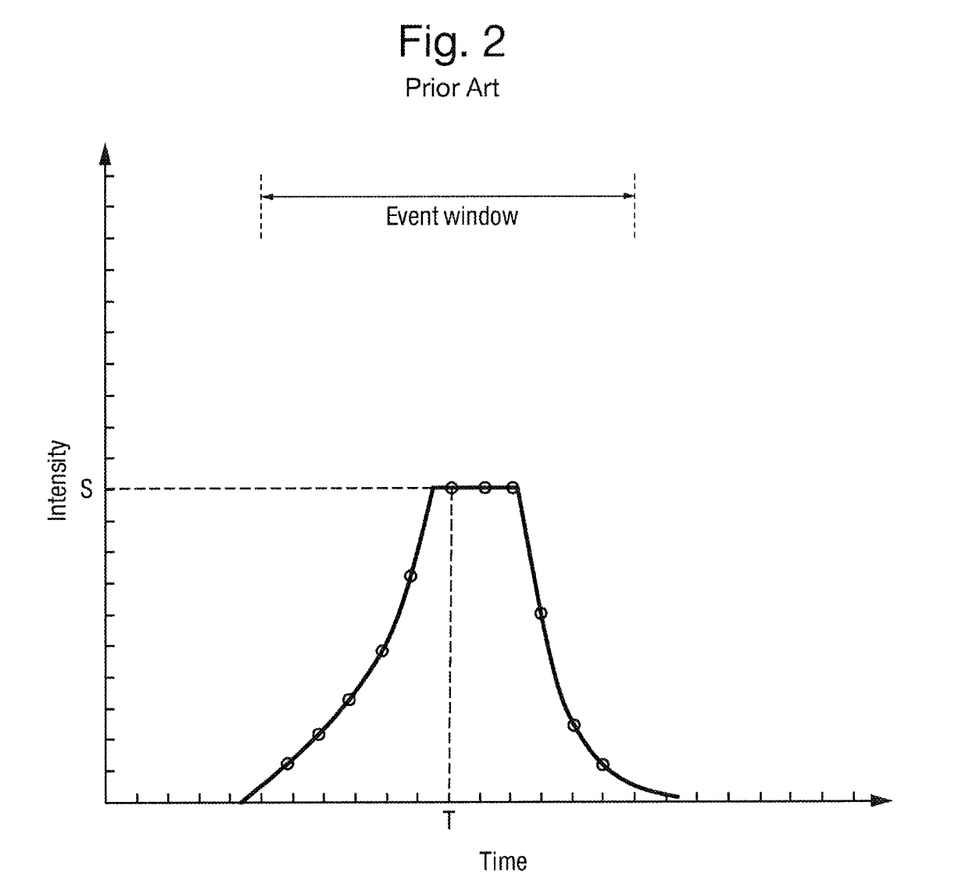
FIG. 2 shows an analogue signal which is beyond the vertical range of the ADC.

FIG. 2 shows an analogue signal which is saturated i.e. the intensity of the ion peak is beyond the vertical range S of the ADC. As a result, a choice must be made as to which time T is assigned to the maximum determined intensity S since there are multiple points which all have the same maximum (saturated) intensity S. In the particular example shown in FIG. 2 the first saturated bin is chosen. However, such an approach leads to a systematic shift to low arrival times. An improvement can be made by choosing the midpoint of a saturated sequence of time bins where an odd number of bins are in saturation. However, such an approach is still not ideal and does not address the problem of an even number of saturated bins.

In principle this limitation can be generalised and the problem may be extended more generally to the analysis of unsaturated data where the peak top is split evenly between two (or more) bins leading to the same decision making problem. Additional problems include the hard limit for the assigned intensity as the events enter saturation resulting in a response versus concentration curve as shown in FIG. 3.

Figure 3:
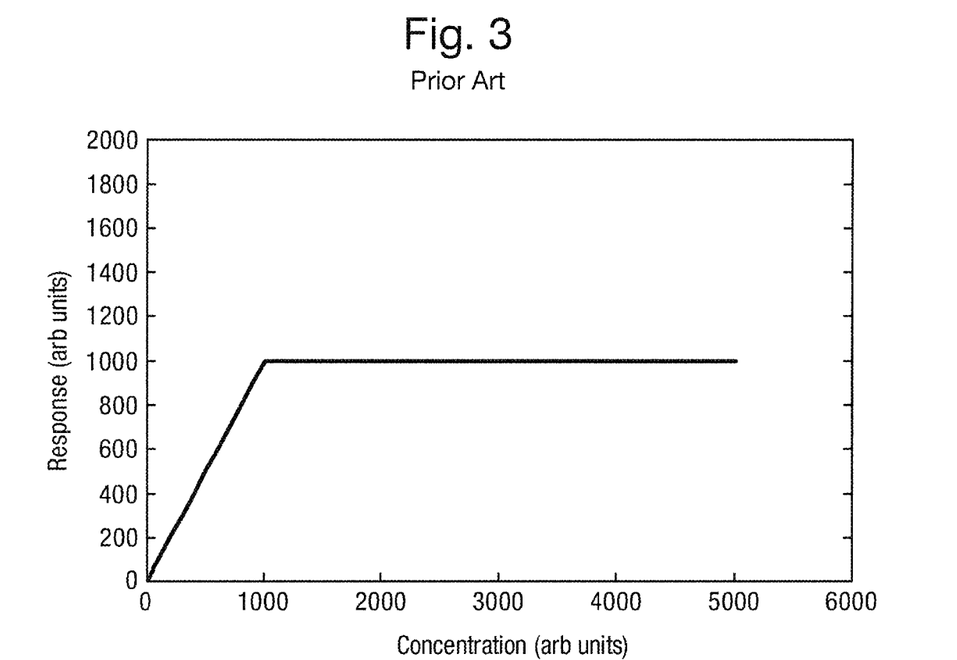
FIG. 3 shows how the response of a conventional ion detector system increases and then saturates as the concentration increases.

The numbers shown in FIG. 3 are arbitrary and are given for illustrative purposes only. It is apparent that as the concentration increases, the response initially increases in a linear manner until the response equals the amplitude saturation limit of the ADC which in this particular case is 1000 arbitrary units. At the saturation limit of the ADC the response becomes independent of concentration as all concentrations result in the same maximum response of 1000.

The approach illustrated in FIG. 3 can be improved by using peak top interpolation routines to calculate the most probable peak top time and intensity. However, such approaches are limited in their applicability due to e.g. noise effects.

Figure 4:
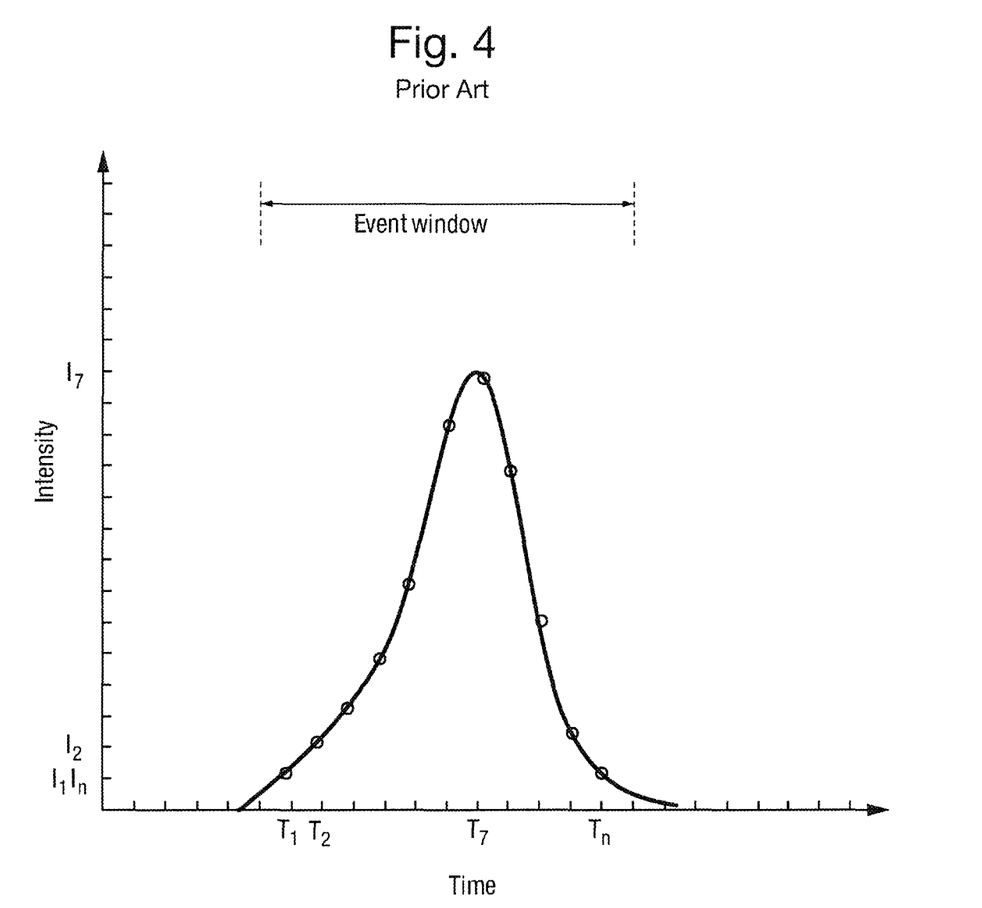
FIG. 4 illustrates a known method of using intensity and time pairs within an event window to calculate the average time and total area (i.e. signal) for an ion arrival event.

Various improvements to the peak top approach of assigning time and intensity values are known. FIG. 4 illustrates a known centroiding technique of measuring the area of an ion peak rather than measuring the maximum intensity. According to the known technique all the measured ADC pairs of intensity and times values (i.e. $I_1$, $T_1$ . . . . $I_n$, $T_n$) within an event window are used to calculate an average time and a total area (i.e. signal) for the ion arrival event.

The approach of measuring the area of an ion peak rather than the maximum intensity results in average time calculations that are precise to less than an ADC bin width. Such an approach results in an improvement in mass accuracy, mass precision and resolution compared with measuring the maximum intensity of the ion peak. The use of multiple points also serves to average down the relative background noise effects (assuming the noise is random) allowing the detection system to run at lower gains thereby further improving the dynamic range.

The approach of measuring the area of an ion peak rather than measuring the maximum height of the ion peak is particularly advantageous when the detector is in saturation as will now be discussed with reference to FIG. 5. For illustrative purposes only a mass spectral peak shape was simulated as an isosceles triangle and was normalised to give a response at the onset of saturation which was equal to that shown in FIG. 3. As can be seen from FIG. 5, determining the area of an ion peak rather than determining the maximum height of the ion peak results in an improved response as indicated by the dashed line. It is apparent that when measuring the area of an ion peak that the response continues to increase when in comparable circumstances the approach of measuring the height of the ion peak has reached the maximum value. This is due to the fact that the area of the resultant trapezoid continues to increase and can be measured even though the increase in the (saturated) height can not be measured.

Whilst peak detecting centroiding ADCs exhibit significant advantages over other forms of peak detection they nonetheless suffer from a number of limitations.

One particular problem is that the dynamic range of an ADC can be a performance limiting factor for experiments with short acquisition times such as those encountered when coupling an ion mobility spectrometer or separator ("IMS") to a Time of Flight mass analyser.

Advantageously, the preferred embodiment as will be discussed in more detail below significantly improves the dynamic range of peak detecting centroiding ADCs.

According to the preferred embodiment additional information contained in the data within an event window is preferably used to correct the determined response (area) of an ion arrival event and/or to correct the assigned time of the event when the detector is suffering from saturation.

In order to illustrate aspects of the preferred embodiment a Time of Flight mass spectrometer was simulated having an 8 bit peak detecting centroiding ADC operating at 3 GHz sampling frequency, with an arrival time distribution of 1.1 ns and an analogue detector pulse width of 1 ns. The mean analogue pulse height was set to 15 bits and the standard deviation in pulse height (pulse height distribution) was set to 2 bits. The ion arrival rate was varied from 1 ion per push to 200 ions per push.

Figure 6:
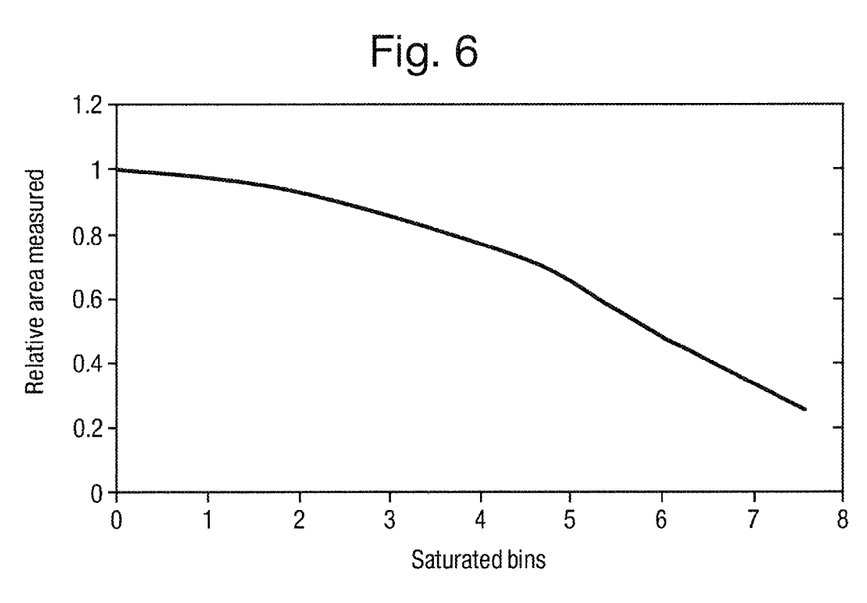
FIG. 6 shows how the measured relative area of an ion peak may vary with the number of saturated time bins according to an embodiment of the present invention.

Using the above simulation the proportion of the area of the peak calculated from the ADC was plotted versus the number of bins in saturation within an event window and is shown in FIG. 6.

FIG. 6 shows the nature of the relationship between the number of saturated bins within an event window and the proportion of the area of the ion peak measured. The preferred embodiment seeks to improve the dynamic range by correcting the peak area measurement based upon the number of saturated bins per event per push. Such an approach will be described below in more detail with reference to FIG. 7.

Figure 7:
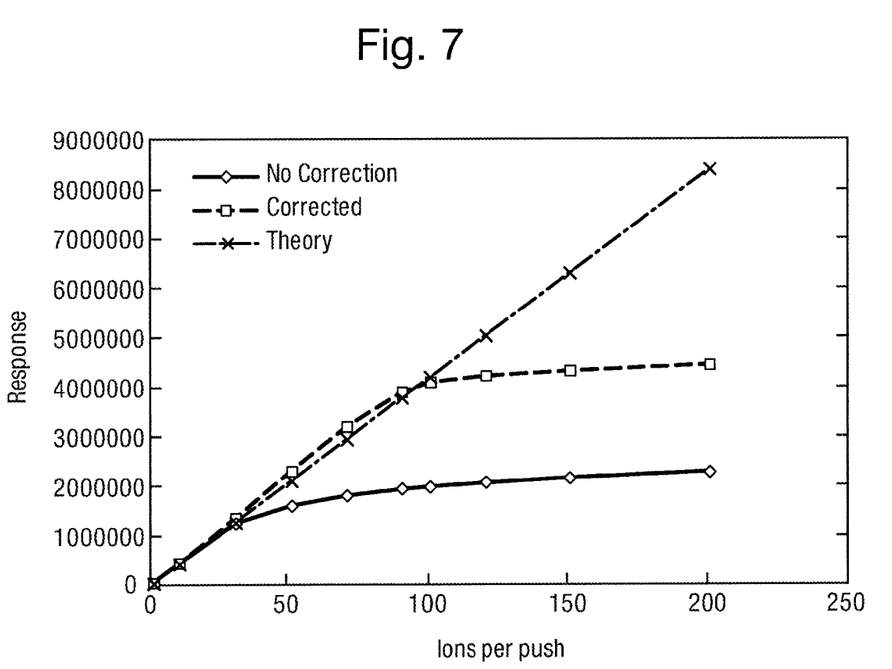
FIG. 7 shows how the preferred embodiment results in a significantly improved dynamic range compared with conventional methods.

FIG. 7 shows experimental results which were obtained wherein individual Time of Flight events were peak detected and centroided in a conventional manner.

The area measurement of each event was then corrected in accordance with the preferred embodiment of the present invention by a value dependent upon the number of saturated bins determined to be present within each event window. The corrected events were then combined to provide a final composite mass spectrum.

The ions per push were varied from 1 to 200 and the response is shown in FIG. 7. As can be seen from FIG. 7, the approach according to the preferred embodiment which is represented by square shaped data points results in a significant improvement in the linear dynamic range by approximately a factor of x3-4 compared with the conventional approach represented by diamond shaped data points. The theoretical ideal relationship between the number of ions per push and the response is also illustrated.

It is apparent that the approach according to the preferred embodiment is particularly useful in correcting time or mass measurement errors due to saturation effects.

The correction factors which are utilised may be determined from multiple sources of information including but not restricted to the number of saturated bins within an event window, the area measured within an event window, width ratios at different heights within event windows, skew and kurtosis measurements within an event window and differential measurements within an event window ($1^{st}$ order/$2^{nd}$ order differential).

More than one source of information may be combined to determine the appropriate correction factor.

The preferred device may be operated with multi gain ADC systems including gain switching systems.

The preferred device may be operated with multi anode detector ADC systems.

The preferred device may be operated with a multi transmission instrument ADC system (pDRE/feedback transmission control) i.e. with a programmable Dynamic Range Enhancement lens using feedback control.

The preferred device has particular utility for Time of Flight mass spectrometers combined with other fast separation techniques such as ion mobility spectrometers or separators ("IMS").

Figure 8:
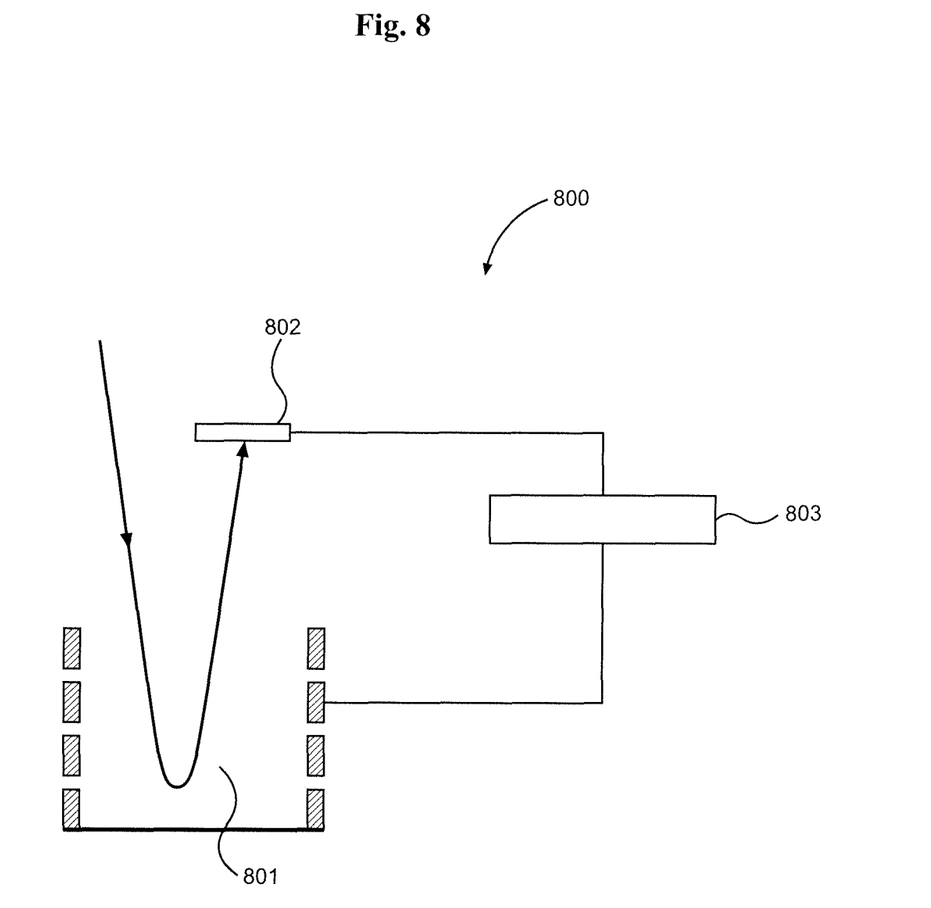
FIG. 8 schematically illustrates a mass spectrometer comprising a time of flight region, an ion detector and a control system.

According to another aspect of the present invention there is provided a mass spectrometer 800, schematically shown in FIG. 8, comprising:
- a time of flight region 801 and an ion detector 802; and
- a control system 803 arranged and adapted:
  (i) to pulse first ions into the time of flight region and to detect the first ions using the ion detector;
  (ii) to digitize a first signal output from the ion detector to produce a first digitized signal, to determine a first area $A_1$ and optionally a first ion arrival time $T_1$ of a first ion peak in the first digitized signal and to determine a first corrected area $A'_1$ of the first ion peak based upon two or more factors;
  (iii) to pulse second ions into the time of flight region and to detect the second ions using the ion detector; and
  (iv) to digitize a second signal output from the ion detector to produce a second digitized signal, to determine a second area $A_2$ and optionally a second ion arrival time $T_2$ of a second ion peak in the second digitized signal and optionally to determine a second corrected area $A'_2$ of the second ion peak based upon two or more factors.

The preferred device can operate with variable transmission instrument ADC systems where the transmission is varied as a function of a second fast separation technique such as ion mobility spectrometry or separation.

According to an embodiment the correction factors which are used may be varied as a function of mass, charge, mass to charge ratio, ion mobility value, chromatographic elution time or combinations thereof.

The correction factors may be determined via calibration routines or by simulations.

The correction factors may be stored in look up tables on the ADC FPGAs or may be calculated in real time.

The preferred approach may be used in conjunction with other signal processing approaches such as de-convolution, area rejection and baseline or background subtraction.

The preferred approach may be utilised with asynchronous, synchronous or trigger interpolated ADCs.

Other less preferred embodiments are contemplated wherein the preferred device may be implemented in mass analysers employing ADCs other than Time of Flight mass spectrometers.

Although the present invention has been described with reference to preferred embodiments, it will be understood by those skilled in the art that various changes in form and detail may be made without departing from the scope of the invention as set forth in the accompanying claims.

The invention claimed is:

1. A method of mass spectrometry comprising:
   pulsing first ions into a time of flight region and detecting said first ions using an ion detector;
   digitizing a first signal output from said ion detector to produce a first digitized signal, determining a first area $A_1$ and a first ion arrival time $T_1$ of a first ion peak in said first digitized signal, determining a degree to which said first ion peak suffers from saturation and determining a first corrected area $A'_1$ of said first ion peak based upon the degree to which said first ion peak was determined to suffer from saturation;
   pulsing second ions into said time of flight region and detecting said second ions using said ion detector; and
   digitizing a second signal output from said ion detector to produce a second digitized signal, determining a second area $A_2$ and a second ion arrival time $T_2$ of a second ion peak in said second digitized signal, determining a degree to which said second ion peak suffers from saturation and determining a second corrected area $A'_2$ of said second ion peak based upon the degree to which said second ion peak was determined to suffer from saturation.

2. A method as claimed in claim 1, wherein said first digitized signal comprises a plurality of first intensity values distributed amongst a plurality of first time or other bins.

3. A method as claimed in claim 2, wherein the step of determining a degree to which said first ion peak suffers from saturation comprises determining the number of first time or other bins having intensity values indicative of saturation.

4. A method as claimed in claim 1, wherein the step of determining a first corrected area $A'_1$ further comprises adjusting or increasing said first area $A_1$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

5. A method as claimed in claim 1, further comprising determining a first corrected ion arrival time $T'_1$ of said first ion peak based upon the degree to which said first ion peak was determined to suffer from saturation.

6. A method as claimed in claim 1, wherein said second digitized signal comprises a plurality of second intensity values distributed amongst a plurality of second time or other bins.

7. A method as claimed in claim 6, wherein the step of determining a degree to which said second ion peak suffers from saturation comprises determining the number of second time or other bins having intensity values indicative of saturation.

8. A method as claimed in claim 1, wherein the step of determining a second corrected area $A'_2$ further comprises adjusting or increasing said second area $A_2$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

9. A method as claimed in claim 1, further comprising determining a second corrected ion arrival time $T'_2$ of said second ion peak based upon the degree to which said second ion peak was determined to suffer from saturation.

10. A method as claimed in claim 1, further comprising:
    pulsing third ions into said time of flight region and detecting said third ions using said ion detector; and
    digitizing a third signal output from said ion detector to produce a third digitized signal, determining a third area $A_3$ and a third ion arrival time $T_3$ of a third ion peak in said third digitized signal, determining a degree to which said third ion peak suffers from saturation and determining a third corrected area $A'_3$ of said third ion peak based upon the degree to which said third ion peak was determined to suffer from saturation.

11. A method as claimed in claim 10, wherein said third digitized signal comprises a plurality of third intensity values distributed amongst a plurality of third time or other bins.

12. A method as claimed in claim 11, wherein the step of determining a degree to which said third ion peak suffers from saturation comprises determining the number of third time or other bins having intensity values indicative of saturation.

13. A method as claimed in claim 10, wherein the step of determining a third corrected area $A'_3$ further comprises adjusting or increasing said third area $A_3$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

14. A method as claimed in claim 10, further comprising determining a third corrected ion arrival time $T'_3$ of said third ion peak based upon the degree to which said third ion peak was determined to suffer from saturation.

15. A method as claimed in claim 10, further comprising:
pulsing fourth ions into said time of flight region and detecting said fourth ions using said ion detector; and
digitizing a fourth signal output from said ion detector to produce a fourth digitized signal, determining a fourth area $A_4$ and a fourth ion arrival time $T_4$ of a fourth ion peak in said fourth digitized signal, determining a degree to which said fourth ion peak suffers from saturation and determining a fourth corrected area $A'_4$ of said fourth ion peak based upon the degree to which said fourth ion peak was determined to suffer from saturation.

16. A method as claimed in claim 15, wherein said fourth digitized signal comprises a plurality of fourth intensity values distributed amongst a plurality of fourth time or other bins.

17. A method as claimed in claim 15, wherein the step of determining a degree to which said fourth ion peak suffers from saturation comprises determining the number of fourth time or other bins having intensity values indicative of saturation.

18. A method as claimed in claim 17, wherein the step of determining a fourth corrected area $A'_4$ further comprises adjusting or increasing said fourth area $A_4$ by x %, wherein x is selected from the group consisting of: (i) <10%; (ii) 10-20%; (iii) 20-30%; (iv) 30-40%; (v) 40-50%; (vi) 50-60%; (vii) 60-70%; (viii) 70-80%; (ix) 80-90%; (x) 90-100%; (xi) 100-200%; (xii) 200-300%; (xiii) 300-400%; (xiv) 400-500%; (xv) 500-600%; (xvi) 600-700%; (xvii) 700-800%; (xviii) 800-900%; (xix) 900-1000%; and (xx) >1000%.

19. A method as claimed in claim 15, further comprising determining a fourth corrected ion arrival time $T'_4$ of said fourth ion peak based upon the degree to which said fourth ion peak was determined to suffer from saturation.

20. A mass spectrometer comprising:
a time of flight region and an ion detector; and
a control system arranged and adapted:
(i) to pulse first ions into said time of flight region and to detect said first ions using said ion detector;
(ii) to digitize a first signal output from said ion detector to produce a first digitized signal, to determine a first area $A_1$ and a first ion arrival time $T_1$ of a first ion peak in said first digitized signal, to determine a degree to which said first ion peak suffers from saturation and to determine a first corrected area $A'_1$ of said first ion peak based upon the degree to which said first ion peak was determined to suffer from saturation;
(iii) to pulse second ions into said time of flight region and to detect said second ions using said ion detector; and
(iv) to digitize a second signal output from said ion detector to produce a second digitized signal, to determine a second area $A_2$ and a second ion arrival time $T_2$ of a second ion peak in said second digitized signal, to determine a degree to which said second ion peak suffers from saturation and to determine a second corrected area $A'_2$ of said second ion peak based upon the degree to which said second ion peak was determined to suffer from saturation.

\* \* \* \* \*